United States Patent [19]
Kandori et al.

[11] Patent Number: 5,397,439
[45] Date of Patent: Mar. 14, 1995

[54] METHOD FOR RECOVERING 1,4-BUTANEDIOL

[75] Inventors: Hiroaki Kandori; Ken Siraga, both of Yokkaichi, Japan

[73] Assignee: Mitsubishi Kasei Corporation, Tokyo, Japan

[21] Appl. No.: 163,554

[22] Filed: Dec. 9, 1993

[30] Foreign Application Priority Data

Dec. 10, 1992 [JP] Japan ................... 4-330469

[51] Int. Cl.$^6$ ............................... B01D 3/34
[52] U.S. Cl. ...................... 203/31; 203/71; 203/99; 203/DIG. 19; 568/913; 568/914
[58] Field of Search ............... 203/31, 29, 71, 14, 203/99, DIG. 19, DIG. 16; 568/913, 916, 914, 864; 560/263; 562/608

[56] References Cited

U.S. PATENT DOCUMENTS 4,010,197  3/1977  Toriya et al. .
4,200,501  4/1980  Panek et al. ................... 203/37

FOREIGN PATENT DOCUMENTS 1560694  2/1980  United Kingdom .

OTHER PUBLICATIONS

CA 1037487 Abstract UP AB 93090, Aug. 29, 1978.
CA 112(12):101187C, Klaus Peter et al.

*Primary Examiner*—Virginia Manoharan
*Attorney, Agent, or Firm*—Oblon, Spivak, McClelland, Maier & Neustadt

[57] ABSTRACT

A method for recovering 1,4-butanediol from a hydrolysate obtained by hydrolyzing diacetoxybutane, by (1) supplying the hydrolysate to a first distillation column, distilling off substantially all the amounts of water and acetic acid as the top stream from the first distillation column, and supplying a bottom liquid to a second distillation column, (2) distilling off diacetoxybutane and hydroxyacetoxybutane as the top or upper side stream from of the second distillation column, and circulating the distillates to a hydrolysis zone, while withdrawing crude 1,4-butanediol as a lower side stream in vapor phase from the second distillation column, (3) supplying the crude 1,4-butanediol and hydrogen gas to a hydrogenation reaction zone packed with a hydrogenation catalyst, and (4) supplying the hydrogenation reaction product to a third distillation column, distilling off low boiling point components and withdrawing 1,4-butanediol as the bottom or side stream from the third distillation column.

19 Claims, 1 Drawing Sheet

METHOD FOR RECOVERING 1,4-BUTANEDIOL

The present invention relates to a method for recovering 1,4-butanediol (hereinafter referred to simply as "1,4-BG") from a hydrolysate of 1,4-diacetoxybutane.

1,4-BG is useful as a raw material for e.g. polyester or tetrahydrofuran. Some methods for producing 1,4-BG are known, and one of which comprises acetoxylating butadiene with acetic acid and oxygen to form 1,4-diacetoxybutene, hydrogenating the 1,4-diacetoxybutene to form 1,4-diacetoxybutane and then hydrolyzing the 1,4-diacetoxybutane to obtain 1,4-BG. A purified 1,4-BG is recovered from the hydrolysis product by multi-step distillations. One of which comprises supplying the hydrolysis product to a first distillation column, distilling off substantially all the amounts of water and acetic acid from the top of the column, supplying the bottom liquid to a second distillation column, distilling off an unreacted substance from the top of the second distillation column, circulating the distillate to a hydrolysis step, while distilling the bottom liquid from the second distillation column in a third distillation column to obtain 1,4-BG as a product (Japanese Patent Laid Open No. 19610/1977).

However, it is found difficult to remove small amounts of impurities which are difficult to separate from 1,4-BG by distillation. In recent years, it has been made clear that small amounts of impurities in 1,4-BG cause such a trouble as coloring of a resin or yarn breakage of fiber made from the 1,4-BG. Accordingly, it has been desired to further improve the quality of 1,4-BG.

For removing impurities in 1,4-BG, a method has been proposed which comprises hydrogenating crude 1,4-BG containing such impurities (the main components are believed to be 2-(4'-hydroxybutoxy)tetrahydrofuran, 2-(4'-oxobutoxy)tetrahydrofuran and 1,4-di-(2'-tetrahydrofuroxy)butane) in the presence of a catalyst to convert the impurities to tetrahydrofuran, 1,4-BG and butanol, and then removing them by distillation (Japanese Unexamined Patent Publication No. 197534/1986). Further, precursors of such impurities, e.g. 2-(4'-hydroxybutoxy)tetrahydrofuran, are aldehydes contained in the acetoxylation product, and a method is also known which comprises hydrogenating 1,4-diacetoxybutane in the presence of a catalyst to remove such aldehydes contained therein prior to the hydrolysis (UK Patent No. 1,519,677). To obtain highly pure 1,4-BG from the hydrolysate of diacetoxybutane, it is considered necessary to apply a combination of distillation and hydrogenation steps to such a hydrolysate.

However, when 1,4-BG obtained by conventional distillation of the hydrolysate was subjected to hydrogenation, the catalytic activity of a hydrogenation catalyst was soon lowered, and it was difficult to produce highly pure 1,4-BG constantly.

The present inventors have found that the deterioration of the catalytic activity of the hydrogenation catalyst is attributable to high-boiling impurities in crude 1,4-BG which act as catalyst poisons. Further, it has been found that the above problem can be solved by adopting such a distillation operation that high-boiling impurities will not be included in 1,4-BG to be supplied to the hydrogenation. The present invention has been accomplished on the basis of these discoveries.

Thus, the present invention provides a method for recovering 1,4-butanediol from a hydrolysate obtained by hydrolyzing diacetoxybutane, which comprises:
(1) supplying the hydrolysate to a first distillation column, distilling off substantially all the amounts of water and acetic acid as top stream from the first distillation column, and supplying a bottom liquid to a second distillation column,
(2) distilling off diacetoxybutane and hydroxyacetoxybutane as the top or upper side stream from the second distillation column, and circulating the distillates to a hydrolysis zone, while withdrawing crude 1,4-butanediol as a lower side stream in vapor phase from the second distillation column,
(3) supplying the crude 1,4-butanediol and hydrogen gas to a hydrogenation reaction zone packed with a hydrogenation catalyst to hydrogenate impurities in the crude 1,4-butanediol, and
(4) supplying the hydrogenation reaction product to a third distillation column, distilling off low boiling components and withdrawing 1,4-butanediol as the bottom or side stream from the third distillation column.

BRIEF DESCRIPTION OF THE DRAWING

In FIG. 1, I designates a hydrolytic reactor, II a first distillation column, III a second distillation column, IV a first hydrogenation reactor, V a second hydrogenation reactor, VI a gas-liquid separator, VII a third distillation column, VIII a fourth distillation column, and reference numerals 1 to 19 pipes and streams flowing in the pipes.

Figure 1:
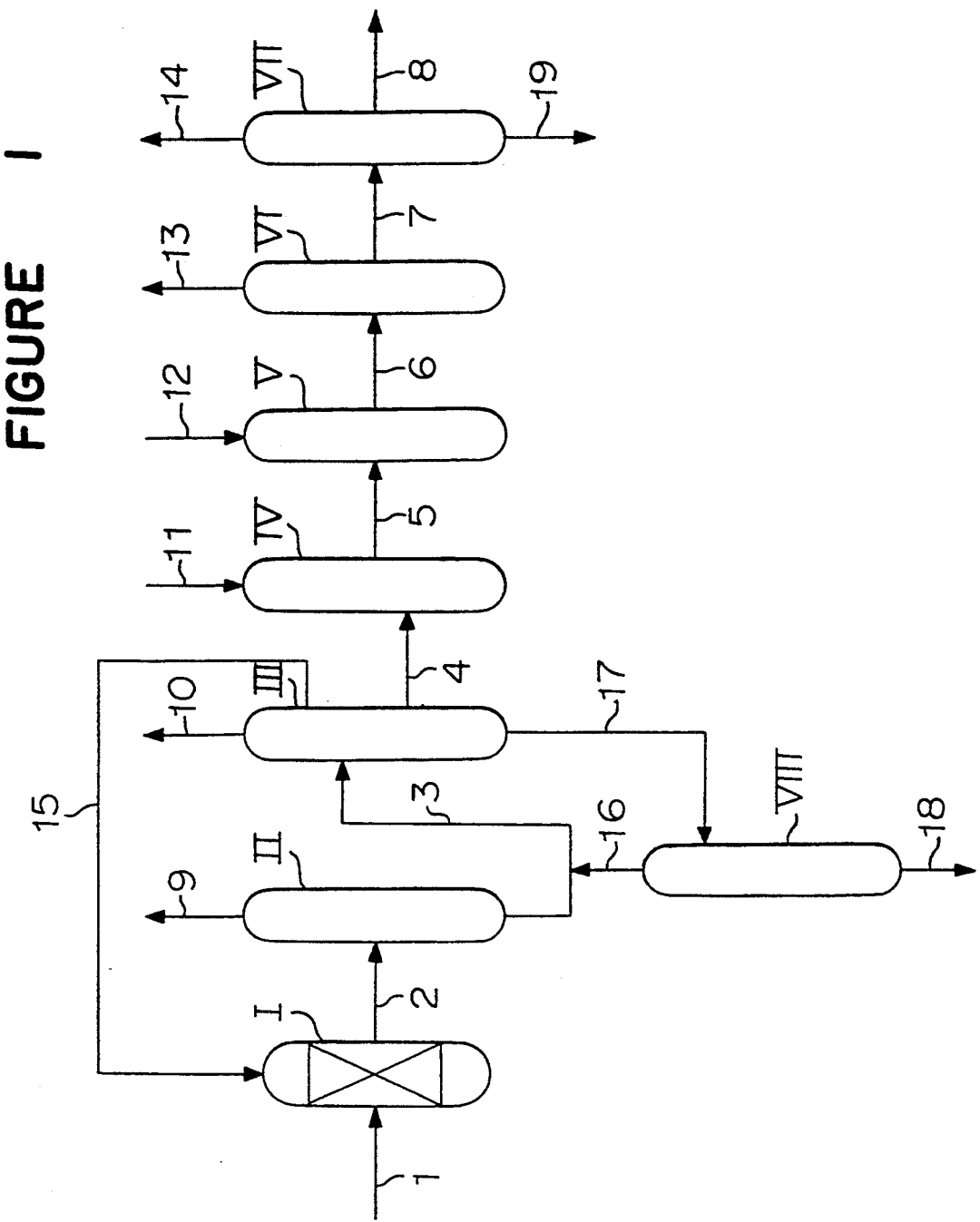
FIG. 1 shows an embodiment of the method for recovering 1,4-BG according to the present invention.

Now, the present invention will be described in detail.

The diacetoxybutane used as raw material in the method of the present invention is produced usually by hydrogenating diacetoxybutene obtained by an acetoxylation of butadiene in the presence of a modified palladium catalyst. Usually, it comprises 1,4-diacetoxybutane as the main component. However, in some cases, it may be a mixture of 1,4-diacetoxybutane with isomers such as 1,2-diacetoxybutane and 1,3-diacetoxybutane. Further, in some cases, it may contain monohydroxyacetoxybutane.

Further, it is possible to employ as raw material for the hydrolysis, a mixture comprising 1,4-diacetoxybutane, 1,4-monohydroxyacetoxybutane and 1,4-BG, obtained by conducting a hydrolysis of 1,4-diacetoxybutane to some extent and then removing water and acetic acid from the reaction product.

For the hydrolysis, it is preferred to employ a cation exchange resin as a catalyst, whereby the reaction rate is high, and formation of by-products such as tetrahydrofuran (hereinafter referred to simply as "THF") is little. As such a cation exchange resin, a sulfonic acid type strongly acidic cation exchange resin is useful, and it may be a so-called gell-type or a porous-type resin. For example, Diaion ® SK1B, SK103, SK106, PK206, PK216 and PK228 manufactured by Mitsubishi Kasei Corporation may be employed.

The hydrolysis is carried out usually at a temperature of from 30° to 110° C., preferably from 40° to 90° C. If the temperature is too low, the reaction rate will be very slow, and a large amount of the catalyst will be required. On the other hand, if the temperature is too high, formation of THF, dihydrofuran, etc. will increase, and the yield of the desired product will be low. The pressure for the reaction is not limited and is usually selected within a range of from atmospheric pressure to 10 kg/cm$^2$G. In the hydrolysis, water serves not only as a reactant but also as a solvent. Accordingly, a stoichiometrically excess amount of water is usually used within a range of from 2 to 100 moles, preferably from 4 to 50 moles, per mole of diacetoxybutane. The reaction may be conducted by various methods. However, it is common to employ a method wherein diacetoxybutane and water are permitted to flow through a fixed bed reactor packed with a strongly acidic cation exchange resin. The reaction mixture obtained here, usually contains from 10 to 40% by weight of 1,4-BG, and the content of by-product 2-(4'-hydroxybutoxy)tetrahydrofuran is from 0.02 to 1% by weight based on the 1,4-BG.

In the present invention, highly pure 1,4-BG is recovered from the reaction product containing 1,4-BG obtained by the above method, by a combination of distillation and hydrogenation. An embodiment for the recovery method will be described with reference to the flow sheet shown in FIG. 1.

Firstly, the hydrolysate from a hydrolytic reactor (I) is supplied to a first distillation column (II). In the first distillation column (II), substantially all the amounts of water and acetic acid will be distilled off as top stream (9) from the top of the column. Here, "distilling off substantially all the amounts" means that the residual amount of acetic acid in the bottom liquid of the column is brought to a level of not higher than 1% of the amount of acetic acid in the hydrolysate supplied. If the bottom temperature of the first distillation column exceeds 210° C., conversion of 1,4-BG to THF will be accelerated. Therefore, the first distillation column is operated usually at a bottom temperature of not higher than 200° C., preferably from 140° C. to 190° C. The pressure at the top of the column is usually from 50 to 150 mmHg. Usually, as the reflux ratio decreases, the consumption of the heat energy may be decreased, but the amount of a diester (diacetoxybutane) or a partial hydrolysate (hydroxyacetoxybutane) discharged together with the distillate from the top of the column increases. However, in the present invention, the reflux ratio in the first distillation column can be set at a level of not higher than 1.0 or even not higher than 0.5 without any trouble in the operation, whereby consumption of the energy can be reduced.

The top stream (9) comprising water and acetic acid may be further purified by distillation and separated into water and acetic acid, which can be reused as starting materials for the hydrolysis and the acetoxylation reaction, respectively.

The bottom liquid (3) of the first distillation column (II) is supplied to a second distillation column (III), whereby a distillate comprising diacetoxybutane, 1,4-BG, hydroxyacetoxybutane, etc., will be obtained from the top or from an upper side part of the column (III). To avoid the formation of THF, the operation temperature of the second distillation column (III) is also required to be controlled so that the bottom temperature is usually not higher than 220° C., preferably from 190° to 210° C. The pressure at the top of the column is usually from 150 to 180 mmHg.

When the diacetoxybutane, the raw material of hydrolysis, contains a 1,2-isomer or a 1,3-isomer in addition to the 1,4-isomer, the bottom liquid (3) of the first distillation column (II) to be supplied to the second distillation column (III) will contain, 1,2-isomers or 1,3-isomers of diacetoxybutane, hydroxyacetoxybutane and butanediol in addition to 1,4-isomers. In such a case, it is preferred that in the second distillation column (III), the fraction containing the 1,2- or 1,3-isomers as the main components is obtained as a distillate (10) from the top of the column, the fraction containing 1,4-isomers of diacetoxybutane and hydroxyacetoxybutane is obtained as an upper side stream (15), and 1,4-BG is withdrawn as the bottom liquid (17). Otherwise, 1,2-, 1,3- and 1,4-isomers of diacetoxybutane and hydroxyacetoxybutane may be recovered together as a distillate (10) from the top of the second distillation column (III), and then they may be separated from one another. In any case, the recovered fraction comprising 1,4-diacetoxybutane and 1,4-hydroxyacetoxybutane as the main components, is circulated to the step of hydrolysis. By feeding a partial hydrolysate formed by such hydrolysis and 1,4-butanediol again to the hydrolysis step, the hydrolysis can be carried out in a uniform liquid phase, whereby it is not only possible to improve the yield, but also the reaction can be conducted smoothly.

On the other hand, in the method disclosed in above-mentioned Japanese Unexamined Patent Publication No. 19610/1977, a crude 1,4-BG fraction from the second distillation column (III), is withdrawn as a bottom liquid. Whereas, the method of the present invention is characterized in that a crude 1,4-BG fraction is withdrawn in a vapor phase as a lower side stream (4). Here, the "upper" and "lower" of the side stream may be defined such that a fraction withdrawn from a position higher than the feed position where the bottom liquid from the first distillation column is supplied, is regarded as an upper side stream, and a fraction withdrawn from a position lower than the feed position, is regarded as a lower side stream. Further, the feed position is usually at an intermediate portion of the distillation column. Since the crude 1,4-BG fraction is withdrawn in a vapor phase from a position of such a lower side part, the content of high-boiling impurities in the crude 1,4-BG fraction can be reduced as compared with the case where it is withdrawn in a liquid phase. The reason is such that as between the liquid phase on a column plate and the vapor phase in an equiblium relation therewith, the vapor phase contains a less amount of high-boiling impurities than the liquid phase.

Further, the bottom liquid (17) of the second distillation column (III) contains a large amount of high boiling components, and therefore may be discharged out of the system. However, the main component of the bottom liquid (17) is 1,4-BG in usual cases. Therefore, the recovery rate of 1,4-BG can be improved by supplying the bottom liquid (17) to a fourth distillation column (VIII) or to a thin film evaporator, and recycling the vapor fraction (16) to the second distillation column (III).

Then, in the present invention, the crude 1,4-BG fraction withdrawn in a vapor phase as the lower side stream of the second distillation column (III), is supplied to a hydrogenation reaction zone, whereby impurities in the crude 1,4-BG are subjected to hydrogenolysis.

The crude 1,4-BG contains various aldehydes and acetals as impurities. The details of aldehydes and acetals are not fully examined, but they include 4-hydroxy-1-butanal and 1,4-butanedial corresponding to mono- and di-aldehyde of 1,4-BG. Further, they include 2-(4'-hydroxybutoxy)tetrahydrofuran (hereinafter referred to simply as BGTF) as an adduct of dihydrofuran and 1,4-BG, 2-(4'-oxobutoxy)tetrahydrofuran (hereinafter referred to simply as BDTF) as an adduct of dihydrofuran and 4-hydroxy-1-butanal, and 1,4-di-(2'-tetrahydrofuroxy)butane (hereinafter referred to as BGDTF).

Such impurities are contained in the crude 1,4-BG usually in an amount of from 0.001 to 2% by weight. As an index of the total amount of such aldehydes and acetals, a carbonyl value may be used. The carbonyl value is represented in mg·KOH/g, which is determined by potentiometric titration, by potassium hydroxide, of an imine hydrochloride formed by a reaction of aldehydes or acetals with hydroxyamine hydrochloride. The carbonyl value of the crude 1,4-BG is usually at a level of from 2 to 20 mg·KOH/g.

The catalyst to be used for the hydrogenation reaction, is not limited. However, it is common to use a catalyst having one or more metals such as Pd, Pt, Ni, Ru, Fe, Os, Rh, Ir, Cr, Mo, W and V supported on a carrier. As the carrier for such a hydrogenation catalyst, activated carbon, alumina, silica gel, silica alumina, clay, borxite, magnesia, diatomaceous earth or pumice can, for example, be used. Particularly preferred is activated carbon or silica.

Depending upon the type of the active component of the hydrogenation catalyst, a difference is observed in the hydrogenation characteristics to impurities, and for decomposition of acetals such as BGTF, palladium (Pd) is preferred. Likewise, for hydrogenation of aldehydes, ruthenium (Ru) is preferred. Accordingly, it is preferred to conduct hydrogenation in two stages by disposing a reactor (IV) packed with a Ru catalyst and a reactor (V) packed with a Pd catalyst in series as shown in FIG. 1. Of course, in some cases, use of either the Pd catalyst or the Ru catalyst will suffice depending upon the composition of impurities. In the present invention, it is preferred from the viewpoint of an industrial process to include at least a hydrogenation reaction step using a palladium catalyst.

Hydrogen to be used for the reaction may not necessarily be pure and may be the one diluted with an inert gas. The hydrogen pressure may be at least atmospheric pressure. If a high pressure is employed, an expensive installation will be required. On the other hand, if the pressure is too low, a large amount of the catalyst will be required. Accordingly, a hydrogen partial pressure of from 5 to 20 kg/cm² is preferred. The reaction may be carried out usually at a temperature within a range of from 40° to 250° C. If the temperature is too high, 1,4-BG undergoes decomposition to form low boiling point substances such as butane, butanol and THF. On the other hand, if the temperature is too low, a large amount of the catalyst will be required. Therefore, the temperature is preferably from 80° to 180° C.

By the hydrogenation reaction, aldehydes and acetals in the crude 1,4-BG are converted to compounds which can readily be separated from 1,4-BG by distillation. Namely, BGTF, BDTF and BGDTF will be converted to THF, 1,4-BG, butanol, ditetramethylene glycol, etc. by hydrogenation.

The hydrogenation reaction products are usually transferred to a gas-liquid separator (VI) maintained under atmospheric pressure and subjected to gas-liquid separation. The liquid phase portion (7) is rectified by distillation in a third distillation column (VII). Also in this case, to suppress formation of by-products such as THF, the conditions for operation of the distillation column are set so that the bottom temperature will be usually not higher than 220° C., preferably from 140° to 210° C. The pressure at the top of the column is usually from 30 to 60 mmHg. 1,4-BG product is usually withdrawn as a side stream, preferably as a lower side stream, from the third distillation column (VII). From the top of the column, top stream (14) comprising low boiling components such as water, THF and butanol is distilled off, and bottom stream (19) comprising high boiling components is withdrawn from the bottom. In some cases, distillation in this third column (VII) may be conducted with a plurality of distillation columns.

Further, in each of the above described distillation operations, if oxygen enters in the distillation column, by-products such as 2-hydroxytetrahydrofuran and 4-hydroxybutylaldehyde will be formed, and they are hardly separable by distillation from 1,4-butanediol, since they have boiling points close to 1,4-butanediol. Therefore, it is advisable to prevent inclusion of oxygen as far as possible, and the oxygen partial pressure at the top of each distillation column should be maintained usually at a level of not higher than 10 mmHg, preferably not higher than 5 mmHg.

According to the present invention, the content of 2-(4'-hydroxybutoxy)tetrahydrofuran as an impurity in 1,4-BG as a final product can be suppressed to a level of not higher than 0.2% by weight.

Now, the present invention will be described in further detail with reference to Examples. However, it should be understood that the present invention is by no means restricted to such specific Examples. In the following Examples, "parts" and "%" mean "parts by weight" and "% by weight", respectively. Further, the analytical values are those measured by gas chromatography for a period of five days after initiation of the operation under a steady condition, unless otherwise specified. The Roman numerals and the Arabic numerals in brackets indicate the apparatus and the pipes and streams flowing in the pipes shown in FIG. 1.

To the reactor (I) packed with 12 l of strongly acidic cation exchange resin Diaion ® SKIB (manufactured by Mitsubishi Kasei Corporation), a 1, 4-diacetoxybutane-containing solution having the composition as identified in Table 1, was supplied at a rate of 67.6 parts/hr and a 28% acetic acid aqueous solution was supplied at a rate of 32.4 parts/hr (1), and hydrolysis was carried out at a reaction temperature of 50° C. The composition of resulted hydrolysate other than water was as shown in Table 1.

TABLE 1

| Components | Composition of raw material (%) | Composition of hydrolysate (%) |
|---|---|---|
| 1,4-diacetoxybutane | 75.9 | 8.0 |
| 1,4-hydroxyacetoxybutane | 5.2 | 32.5 |
| 1,4-BG | 0.5 | 27.8 |
| 1,2-diacetoxybutane | 8.3 | 0.7 |
| 1,2-hydroxyacetoxybutane | 4.3 | 1.8 |
| 1,2-butanediol | 0.2 | 4.7 |
| Acetic acid | 2.2 | 20.4 |
| Others | 3.4 | 4.1 |

This hydrolysate (2) was supplied to the first distillation column (II), and distilled therein. The first distillation column (II) was made of SUS316 and had an inner diameter of 200 mm, and Raschig rings made of SUS316 were packed thereon, so that the packed layer height was 3,000 mm. The hydrolysate (2) was fed at 500 mm below the top of the packed layer, and the operation was conducted under a top pressure of 70 mmHg at a reflux ratio of 0.5 at a bottom temperature of 160° C., whereby top stream (9) comprising water, acetic acid and very small amounts of low boiling components was distilled off from the top, and the bottom liquid (3) was supplied to the second distillation column (III).

The second distillation column (III) was made of SUS304 and had an inner diameter of 100 mm, and McMahon Packing made of SUS304 was packed therein so that the packed layer height was 5,000 mm. An upper side stream (15) was withdrawn at 1,000 mm below the top of the packed layer, and the bottom liquid (3) was fed at 1,000 mm below the withdrawing point of the upper side stream (15). Further, a lower side stream (4) was withdrawn at 1,000 mm below the feeding point of the bottom liquid (3). The lower side stream was withdrawn in vapor phase. In this second distillation column, the bottom liquid (3) from the first distillation column was subjected to distillation under a top pressure of 300 mmHg at a reflux ratio of 80 at a bottom temperature of 210° C.

From the top, a fraction comprising 9.5% of 1,2-diacetoxybutane, 25.2% of 1,2-hydroxyacetoxybutane and 65.3% of 1,2-butanediol, was distilled off. Further, as the upper side stream (15), a fraction comprising 0.4% of 1,2-diacetoxybutane, 0.9% of 1,2-hydroxyacetoxybutane, 2.4% of 1,2-butanediol, 15.9% of 1,4-diacetoxybutane, 64.1% of 1,4-hydroxyacetoxybutane and 11.4% of 1,4-BG, was withdrawn. This fraction was circulated to the above-mentioned hydrolysis zone (I) as a part of the raw material.

Further, as the lower side stream (4), crude 1,4-BG was withdrawn in a vapor phase.

Then, 1,874 parts/hr of the above crude 1,4-BG containing 2.05% of BGTF and 0.1% of impurities including BDTF, BGDTF and high boiling point components and having a carbonyl value of 6.2 mg·KOH/g and purity of 97.5%, was supplied together with 0.5 part/hr of hydrogen, to two hydrogenation reactors (IV) and (V) disposed in series. Both hydrogenation reactors (IV) and (V) had an inner diameter of 500 mm and a height of 1,300 mm. The first hydrogenation reactor (IV) was packed with a catalyst having 0.5% of ruthenium supported on activated carbon, and the second hydrogenation reactor (V) was packed with a catalyst having 1.0% of palladium supported on activated carbon. Each reactor was operated under a pressure of 9.5 kg/cm$^2$ at a temperature of 100° C.

The hydrogenation reaction product (6) was supplied to a gas-liquid separator (VI), wherein an excess hydrogen (13) was separated from the reaction mixture. The reaction mixture (7) was supplied to a third distillation column (VII).

The third distillation column (VII) was made of carbon steel and had an inner diameter of 100 mm, and McMahon Packing made of carbon steel was packed therein so that the packed layer height was 2,000 mm. The pipe for the side stream (8) was made of SUS304.

The side stream (8) was withdrawn at 300 mm below the top of the packed layer, and the reaction mixture (7) was fed at 700 mm below the outlet of the side stream (8). Distillation was carried out under a top pressure of 200 mmHg at a reflux ratio of 90 at a bottom temperature of 215° C.

Purified 1,4-BG withdrawn as the side stream (8) was analyzed on the 5th day and the 30th day after the initiation of steady operation, and the results are shown in Table 2.

EXAMPLE 2

The operation was carried out in the same manner as in Example 1 except that in Example 2, the first hydrogenation reactor (IV) packed with a ruthenium catalyst was not provided, and the results are shown in Table 2.

COMPARATIVE EXAMPLE 1

The operation was carried out in the same manner as in Example 1 except that the crude 1,4-BG fraction was withdrawn from the bottom of the second distillation column instead of withdrawing the crude 1,4-BG fraction as the lower side stream. Namely, the operation was carried out in the same manner as in Example 1 except that the crude 1,4-BG withdrawn from the bottom (purity: 96.8%, BGTF: 2.50%, impurities including BDTF, BGDTF and high boiling components: 0.98%, carbonyl value: 13.7 mg·KOH/g) was supplied to the hydrogenation reactor (IV). The results are shown in Table 2.

COMPARATIVE EXAMPLE 2

The operation was carried out in the same manner as in Comparative Example 1 except that in Comparative Example 2, the hydrogenation reaction step was omitted. The results are shown in Table 2.

TABLE 2

|  | Mode of withdrawal of crude 1,4-BG from the second distillation column | Hydrogenation | Analysis | Purity of 1,4-BG (%) | Amount of BGTF (%) | Carbononyl value (mg.KOH/g) |
|---|---|---|---|---|---|---|
| Example 1 | Side stream in vapor phase | Ex1 First step: Ru Second step: Pd | 5th day 30th day | 99.7 99.7 | 0.18 0.17 | 0.5 0.5 |
| Example 2 | Side stream in vapor phase | Ex2 Only one step: Pd | 5th day 30th day | 99.6 99.6 | 0.18 0.18 | 0.6 0.7 |
| Comparative Example 1 | Bottom liquid | Ex1 First step: Ru Second step: Pd | 5th day 30th day | 99.7 98.5 | 0.35 0.95 | 0.9 3.0 |
| Comparative Example 2 | Bottom liquid | Nil | 5th day | 97.5 | 2.05 | 6.1 |

According to the present invention, 1,4-BG of high purity can be produced constantly over a long period of time, and thus the industrial value of the present invention is significant.

What is claimed is:

1. A method for recovering 1,4-butanediol from a hydrolysate comprising water, acetic acid, butanediol, unreacted diacetoxybutane and hydroxyacetoxybutane obtained by hydrolyzing diacetoxybutane, which comprises:

(1) supplying the hydrolysate to a first distillation column, withdrawing a first product containing substantially all the amounts of water and acetic acid as the top stream from the first distillation column, and supplying a bottom liquid to a second distillation column, (2) withdrawing a second product comprising diacetoxybutane and hydroxyacetoxybutane from the top or upper side part of the second distillation column, and circulating the second product to a hydrolysis zone, while withdrawing crude 1,4-butanediol as a lower side stream in vapor phase from the second distillation column, (3) supplying the crude 1,4-butanediol and hydrogen gas to a hydrogenation reaction zone packed with a hydrogenation catalyst, and (4) supplying the hydrogenation reaction product to a third distillation column, withdrawing a third product comprising low boiling point components from the top of the third distillation column, and withdrawing 1,4-butanediol from the bottom or lower part of the third distillation column.

2. The method according to claim 1, which further comprises: supplying a bottom liquid withdrawn from the second distillation column to a fourth distillation column, and supplying a distillate comprising 1,4-butanediol from the top of the fourth distillation column to the second distillation column.

3. The method according to claim 1, wherein the second product comprising diacetoxybutane and hydroxyacetoxybutane is withdrawn from the upper side part of the second distillation column.

4. The method according to claim 1, wherein the bottom temperature of the first distillation column is not higher than 200° C.

5. The method according to claim 1, wherein the amount of residual acetic acid in the bottom liquid recovered from the first distillation column is not more than 1% by weight of the acetic acid in the hydrolysate supplied to the first distillation column.

6. The method according to claim 1, wherein the bottom temperature of the second distillation column is not higher than 220° C.

7. The method according to claim 1, wherein the bottom temperature of the third distillation column is not higher than 220° C.

8. The method according to claim 1, wherein the low boiling point components comprising water, a tetrahydrofuran and butanol are withdrawn from the top of the third distillation column.

9. The method according to claim 1, wherein an oxygen partial pressure at the top of each distillation column is controlled to a level of not higher than 10 mmHg.

10. The method according to claim 1, wherein the hydrogenation reaction is conducted in a single step or multi steps.

11. The method according to claim 1, wherein a palladium and/or ruthenium-supporting catalyst is used as the hydrogenation catalyst.

12. The method according to claim 1, wherein the hydrogenation catalyst is a palladium-supporting catalyst.

13. The method according to claim 1, wherein the hydrogenation reaction comprises a first reaction wherein a ruthenium-supporting catalyst is used and a second reaction wherein a palladium-supporting catalyst is used.

14. The method according to claim 1, wherein the hydrogen partial pressure for the hydrogenation reaction is from 5 to 20 kg/cm$^2$.

15. The method according to claim 1, wherein the temperature for the hydrogenation reaction is from 80 to 180° C.

16. The method according to claim 1, wherein the hydrolysate supplied to the first distillation column, is a mixture obtained by contacting a mixture of diacetoxybutane with from 2 to 100 mole times of water to a cation exchange resin, at a temperature of from 40 to 90° C.

17. The method according to claim 1, wherein the hydrolysate supplied to the first distillation column, contains from 10 to 40% by weight of 1,4-butanediol and further comprises from 0.02 to 1.0% by weight, based on the 1,4-butanediol content, of 2-(4'-hydroxybutoxy)tetrahydrofuran.

18. The method according to claim 17, wherein the content of 2-(4'-hydroxybutoxy)tetrahydrofuran in the 1,4-butanediol product recovered from the third distillation column, is not higher than 0.2% by weight.

19. A method for recovering 1,4-butanediol from a hydrolysate comprising water, acetic acid, butanediol, 2-(4'-hydroxybutoxy)tetrahydrofuran, unreacted diacetoxybutane and hydroxyacetoxybutane obtained by hydrolyzing diacetoxybutane, which comprises:

(1) supplying the hydrolysate to a first distillation column, withdrawing a first product containing substantially all the amounts of water and acetic acid as the top stream from the first distillation column, and supplying a bottom liquid to a second distillation column, (2) withdrawing a second product comprising diacetoxybutane and hydroxyacetoxybutane from the top or upper side part of the second distillation column, and circulating the second product to a hydrolysis zone, while withdrawing crude 1,4-butanediol as a lower side stream in vapor phase from the second distillation column, (3) supplying the crude 1,4-butanediol and hydrogen gas to a hydrogenation reaction zone packed with a hydrogenation catalyst, and (4) supplying the hydrogenation reaction product to a third distillation column, withdrawing a third product comprising low boiling point components from the top of the third distillation column, and withdrawing 1,4-butanediol, which contains 0.2% by weight or less of 2-(4'-hydroxybutoxy)tetrahydrofuran, from the bottom or lower part of the third distillation column.

* * * * *